United States Patent [19]
Dasse et al.

[11] Patent Number: 5,171,216
[45] Date of Patent: Dec. 15, 1992

[54] MULTI-LUMEN CATHETER COUPLING

[75] Inventors: Kurt Dasse, Needham; Scott M. Epstein, Natick; Victor Poirier, Chelmsford, all of Mass.

[73] Assignee: Thermedics, Inc., Woburn, Mass.

[21] Appl. No.: 785,919

[22] Filed: Nov. 4, 1991

Related U.S. Application Data

[63] Continuation of Ser. No. 593,509, Oct. 2, 1990, abandoned, which is a continuation of Ser. No. 399,160, Aug. 28, 1989, abandoned.

[51] Int. Cl.$^5$ .............................................. A61M 3/00
[52] U.S. Cl. ....................................... 604/43; 604/175; 604/283
[58] Field of Search ............... 604/27, 29, 39, 43-45, 604/51, 52, 93, 174-180, 271, 280, 283, 284, 905

[56] References Cited

U.S. PATENT DOCUMENTS

| | | | |
|---|---|---|---|
| 1,696,018 | 12/1928 | Schellberg | 604/43 |
| 4,092,983 | 6/1978 | Silvenko | 604/175 |
| 4,405,320 | 10/1983 | Cracauer et al. | 604/175 |
| 4,496,349 | 1/1985 | Cosentino | 604/175 |
| 4,563,170 | 1/1986 | Aigner | 604/27 |
| 4,578,063 | 3/1986 | Inman et al. | 604/175 |
| 4,654,033 | 3/1987 | Lapeyre et al. | 604/905 |
| 4,668,222 | 5/1987 | Poirer | 604/175 |
| 4,886,502 | 12/1989 | Poirier et al. | 604/175 |
| 4,895,561 | 1/1990 | Mahurkar | 604/43 |
| 4,897,081 | 1/1990 | Poirier et al. | 604/175 |

Primary Examiner—John D. Yasko
Assistant Examiner—Anthony Gutowski
Attorney, Agent, or Firm—Lorusso & Loud

[57] ABSTRACT

A multi-lumen catheter for independent delivery and withdrawal of fluids having an improved leading end to minimize stasis and an improved coupling for connection to externally located infusion and withdrawal tubes. The improved leading end has an ellipsoidally shaped tip with a smooth, uninterrupted surface and, in close proximity to the tip, a port or ports evenly spaced along the length of each lumen in staggered relation between each lumen. The improved coupling is a generally L-shaped, implantable transition device bonded to a percutaneous access device. The overall conformation of the multi-lumen catheter may be either a "U-shape" or an upright "Z-shape." Externally located infusion and withdrawal tubes are in fluid connection with an epidermal end of the transition device and a multi-lumen tube fits snugly over nipples at a subcutaneous end of the transition device.

8 Claims, 11 Drawing Sheets

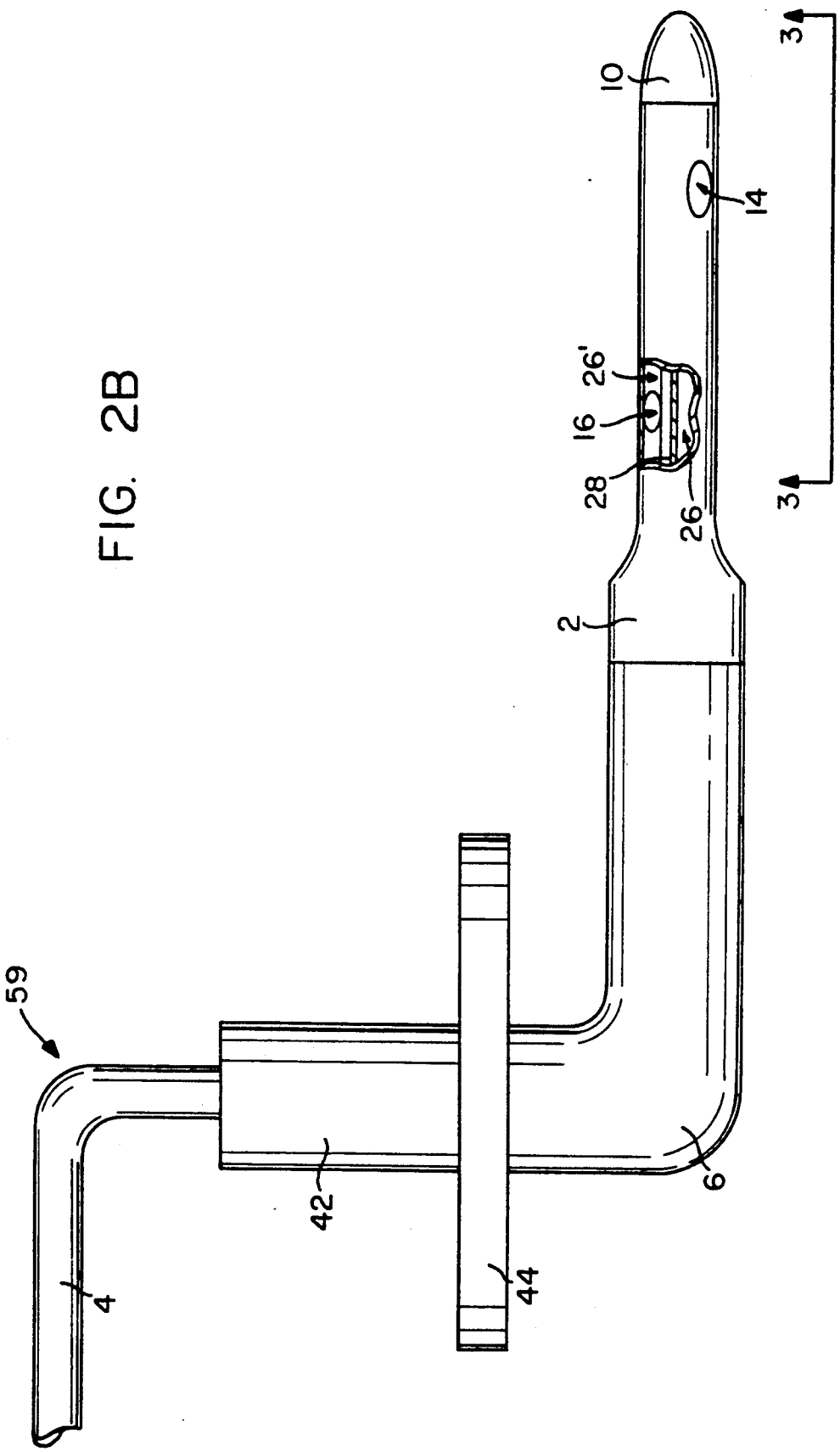

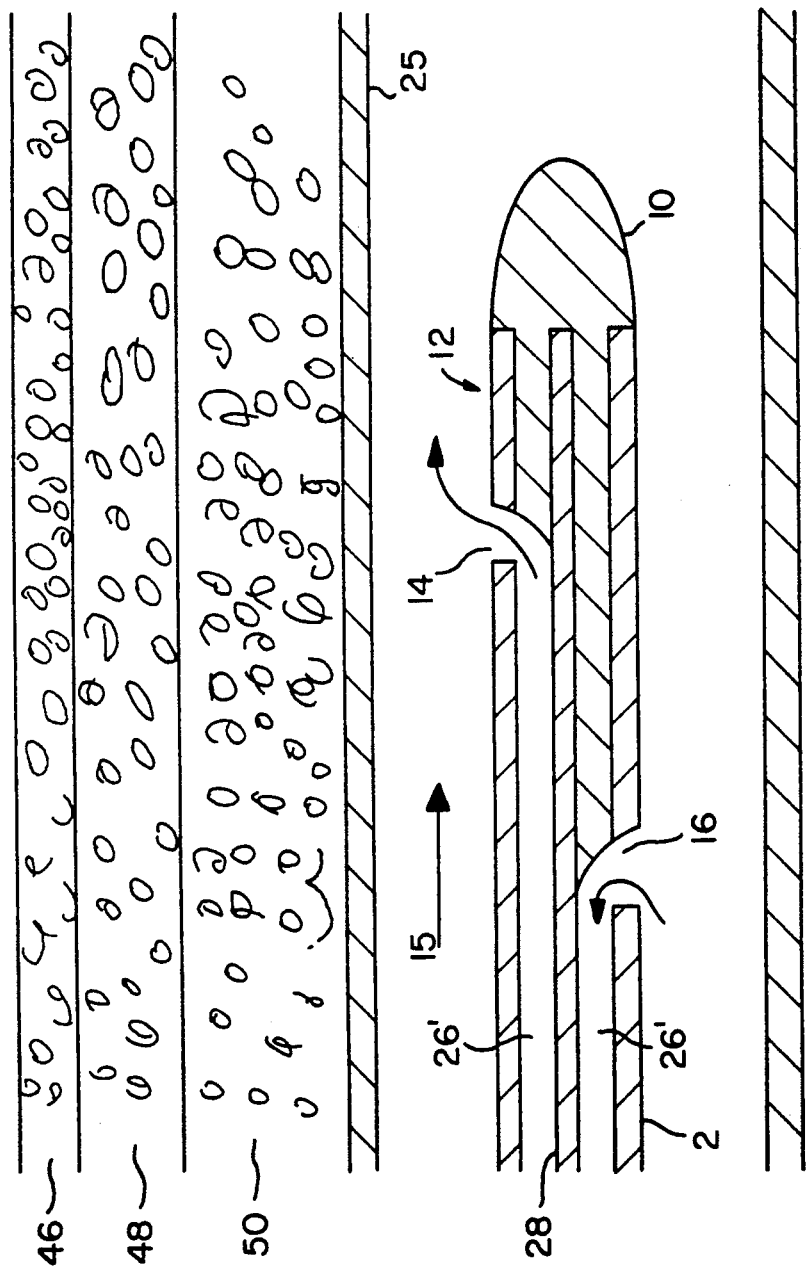

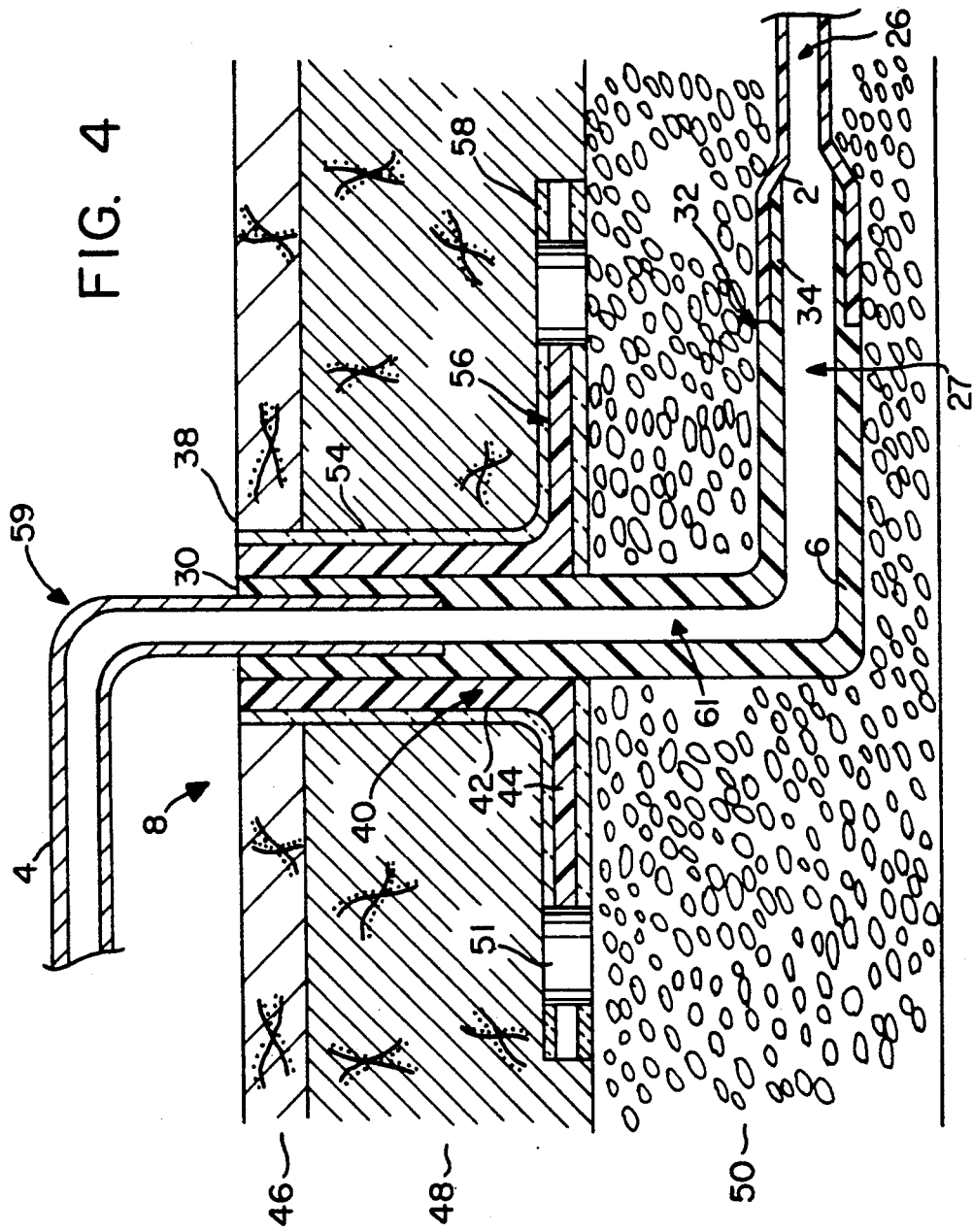

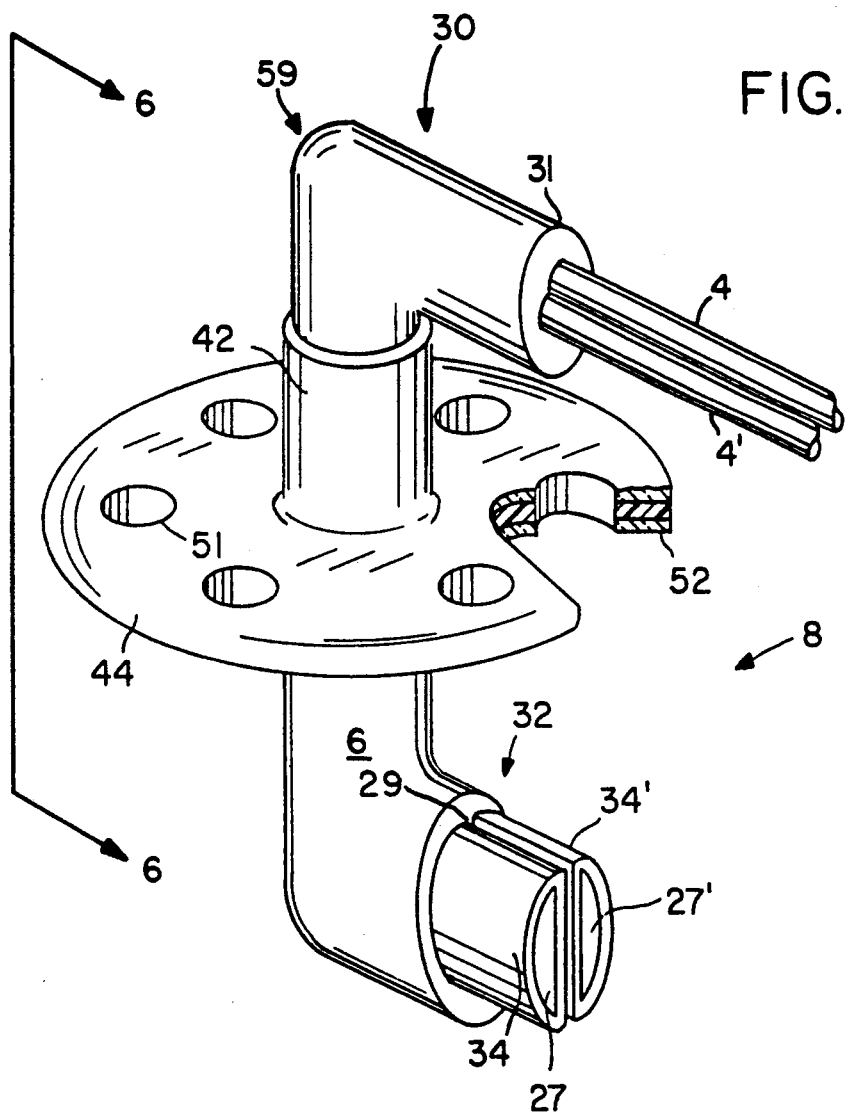

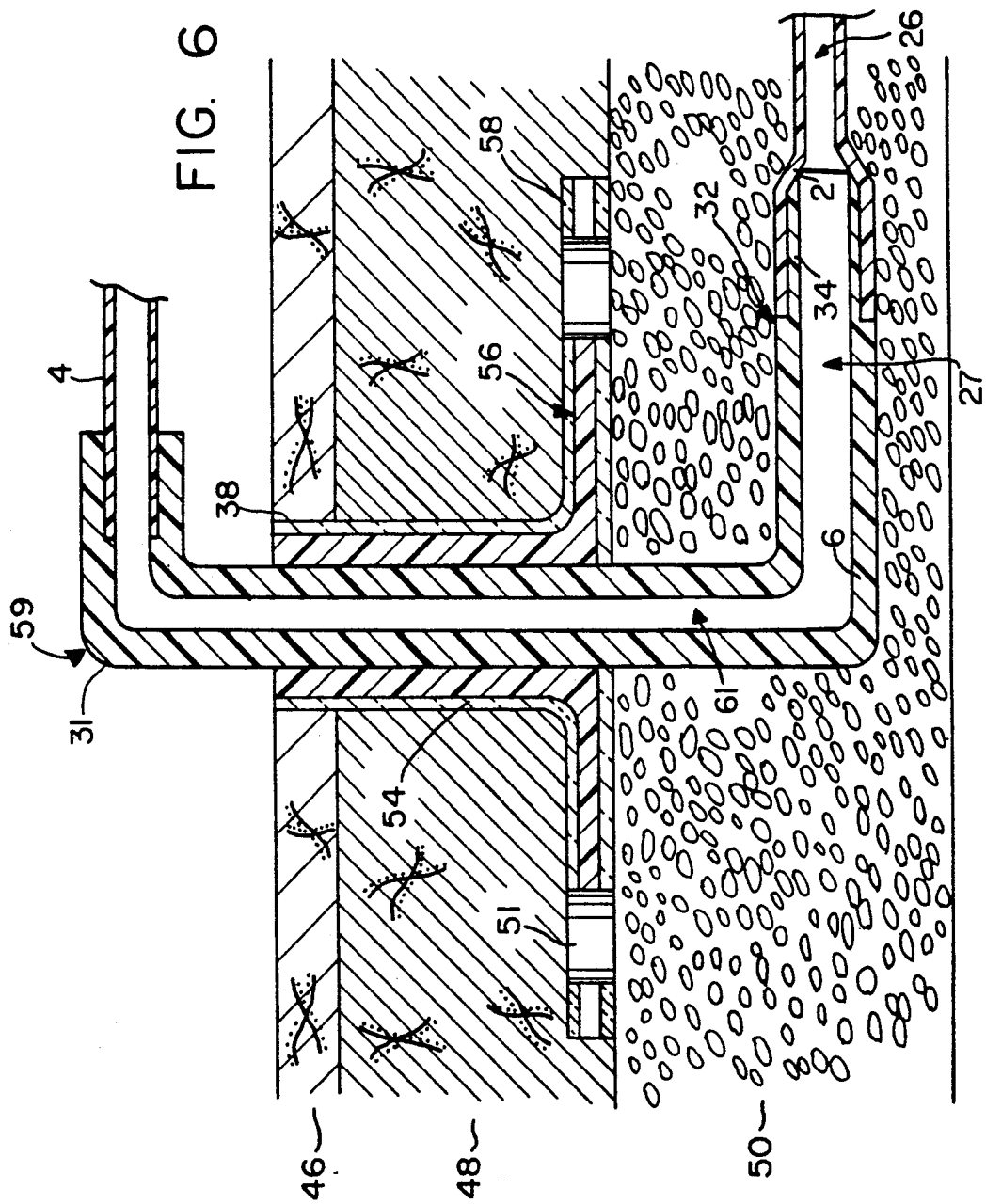

MULTI-LUMEN CATHETER COUPLING

CROSS-REFERENCE TO RELATED APPLICATIONS

This is a file-wrapper-continuation of pending U.S. application Ser. No. 07/593,509, filed Oct. 2, 1990, abandoned, entitled "Multi-Lumen Catheter", (Abandoned) which is a file-wrapper-continuation of U.S. application Ser. No. 07/399,160, filed Aug. 28, 1989, entitled "Multi-Lumen Catheter" (Abandoned).

BACKGROUND OF THE INVENTION

This invention relates to a multi-lumen catheter for the simultaneous infusion and/or withdrawal of fluids from a patient's body.

Catheters having multiple interior lumens are desirable because they reduce the number of tubes which are passed through a patient's skin and ultimately reduce the risk of infection. Such catheters are commonly employed in hemodialysis treatment. When used in this capacity, these catheters are called dual lumen catheters because they typically comprise two lumens: one to withdraw blood from a patient and the other to deliver the treated blood back to the patient.

Other applications for multi-lumen catheters include simultaneous delivery of incompatible drugs to patients. For example, certain cancer treating drugs cannot be delivered through a common catheter lumen due to their incompatibility, although these drugs may be simultaneously delivered into a patient's body. The ability to simultaneously deliver drugs to a patient promotes the efficient discharge of hospital duties. This aspect is especially important in light of the nursing shortage currently plaguing the health care industry.

Several dual lumen catheters exist for hemodialysis treatment. These catheters have an infusion port, a withdrawal port, and a catheter tip all at a distal or leading end of the catheter. The infusion and withdrawal ports permit fluid communication between a patient's body and their respective lumens. A common feature among these catheters is the location of the infusion port at the most distal point on the catheter tip. An example of this configuration is disclosed in U.S. Pat. No. 4,682,978. The purpose of this catheter tip design is to allow insertion and positioning of the catheter within a blood vessel by advancing the catheter over a guide wire. A problem with prior art catheters is that the discontinuous surface of the catheter tip often results in thrombosis in the frontal area. The indenture in the catheter tip due to the infusion port causes slowing of blood flow at the tip, otherwise known as stasis. Although the leading ends of these catheters are, in several instances, tapered to facilitate insertion, the problems associated with the discontinuity of the catheter tip surface are not surmounted.

A second common feature among dual lumen catheters is the location of the withdrawal port in relation to the infusion port. The withdrawal port is generally located upstream from and proximal to the infusion port. The purpose of this configuration is to assure the withdrawal of only untreated blood. One strategy for the separation of the infusion and withdrawal ports involves the blockage of the withdrawal lumen at a distal end while the infusion lumen continues on through the catheter tip as described in U.S. Pat. Nos. 4,098,275; 4,134,402; 4,385,631; 4,403,983; 4,451,252; 4,493,696; 4,453,087; 4,583,968; 4,619,643; and 4,682,978. Another method of achieving this separation is by providing coaxial infusion and withdrawal lumens wherein the core infusion lumen has a longer length than the annular withdrawal lumen as described in U.S. Pat. Nos. 4,096,860; 4,099,528; and 4,202,332. A third configuration which achieves this same effect is a hybrid of the first two configurations wherein the annular withdrawal lumen is blocked at the distal end as described in U.S. Pat. Nos. 4,270,535 and 4,493,696.

Dual lumen catheters described in the prior art typically have three segments: a dual lumen tube, a coupling or transition device, and two single lumen tubes. The coupling provides an interface between the dual lumen tube and the single lumen tubes such that the fluids within each single lumen tube remain separated within the dual lumen catheter. A common coupling device is a "Y-shaped" juncture such as that described in U.S. Pat. No. 4,682,978. A problem with presently available dual lumen catheters is that the dual lumen tube runs in essentially a straight line in alignment with the site at which the catheter first enters a patient's body (the introduction site). This linear configuration leads to a substantial risk of infection at the introduction site. Unfortunately, the infection cannot be avoided by simply bending the dual lumen catheter without compromising the internal structure of the dual lumen tube.

The dual lumen catheters of the prior art also possess percutaneous access devices proximally located along the dual lumen tube to anchor the catheter within the patient during hemodialysis treatment. The coupling device, however, is externally located with respect to the patient's body. A drawback of presently available dual lumen catheters is that the external location of the coupling increases the risk of contamination within the dual lumen tube.

Another drawback of presently available dual lumen catheters is that they cannot remain within a patient for periods of one year or more. This is because the skin adjacent to the percutaneous access device of the implanted catheter does not heal to form a tight barrier to infection. Instead, when a dual lumen catheter is implanted, epidermal cells begin to migrate, each seeking to surround itself completely with other similar cells. Thus the epidermal cells grow alongside of the percutaneous access device in search of sister cells. Deep sinus tracts form and body fluids are exuded at the interface between the percutaneous access device and adjacent tissue thereby forming a bed for infection. If it is not expelled spontaneously, the implanted catheter must be surgically removed to allow the infection to be cured.

It is clear that a more effective device is needed to simultaneously infuse and withdraw fluids from a patient's body. Existing dual lumen catheters possess infusion ports in the catheter tip for advancing the catheter in a patient's body over a guide wire. The location of the infusion port for the axially located lumen causes stasis at the catheter tip and can disrupt the structural integrity of cells lining the body cavity. These catheters are not suitable for long-term applications. Thus, a multi-lumen catheter that minimizes stasis, reduces the risk of infection, and permits long-term skin penetration is desired.

SUMMARY OF THE INVENTION

In accordance with the present invention, it has been discovered that a multi-lumen catheter having a tip with a smooth surface and an ellipsoidal shape minimizes stasis at the leading end. It has also been found that a multi-lumen tube can be coupled with externally located infusion and withdrawal tubes using a transition device having internal lumens. The internal lumens of the transition device can be sharply angled to tunnel the multi-lumen tube in a subcutaneous plane from the introduction site to reduce the risk of infection. In addition, the transition device can be bonded to a percutaneous access device for long-term skin penetration.

Accordingly, the present invention is a multi-lumen catheter for independent delivery and withdrawal of fluids having an improved leading end to minimize stasis and an improved coupling for connection to externally located infusion and withdrawal tubes. The improved leading end has an ellipsoidally shaped tip with a smooth, uninterrupted surface and, in close proximity to the tip, one or more ports evenly spaced along an opposing helical path of each lumen in a staggered relationship. The improved coupling is an "L-shaped," implantable transition device bonded to a percutaneous access device. In one embodiment the externally located infusion and withdrawal tubes are connected to the transition device such that the multi-lumen catheter assumes a "U-shape." In a second embodiment, the external tubes are connected to the transition device in an upright "Z-shape" configuration. The transition device has a multitude of internal lumens. Lumens within the transition device are divided by septa. Each internal lumen of the transition device has a nipple at a subcutaneous end. Externally located infusion and withdrawal tubes are inserted into an epidermal end of the transition device. At the subcutaneous end of the transition device, each nipple fits snugly into a corresponding lumen within a multi-lumen tube.

It is therefore an object of the present invention to provide a multi-lumen catheter that minimizes stasis.

It is another object of the present invention to provide a multi-lumen catheter that reduces the risk of infection.

It is a further object of the present invention to provide a multi-lumen catheter that permits long-term skin penetration.

BRIEF DESCRIPTION OF THE DRAWING

FIG. 2B is a side plan view in partial cross-section of the preferred embodiment of the present invention having only one port in each lumen;

FIG. 3 is a cross-sectional view of the preferred embodiment of a multi-lumen catheter according to the invention in a blood vessel also shown in cross-section taken along the line 3—3 in FIG. 2B showing the infusion and withdrawal ports and the tip;

FIG. 4 is a cross-sectional view of an embodiment of a multi-lumen catheter according to the invention in a blood vessel also shown in cross-section taken along the line 4—4 in FIG. 1;

FIG. 5B is a perspective view of an embodiment of the present invention showing the externally located infusion and withdrawal tubes, the percutaneous access device in partial cross-section, and the transition device with the rigid adaptor forming a "U-shape";

FIG. 6 is a cross-sectional view of an embodiment of a multi-lumen catheter according to the invention in a blood vessel also shown in cross-section taken along the line 5-5 in FIG. 5B;

which corresponds to the cross-sectional profile of the elliptically shaped tip of the catheter;

DESCRIPTION OF THE PREFERRED EMBODIMENTS

At the outset, the present invention is described in its broadest overall aspects with a more detailed description following. The present invention relates to a device for accessing a patient's central venous system. More particularly, the invention relates to a device for the long-term access of the central venous system.

Figure 1:
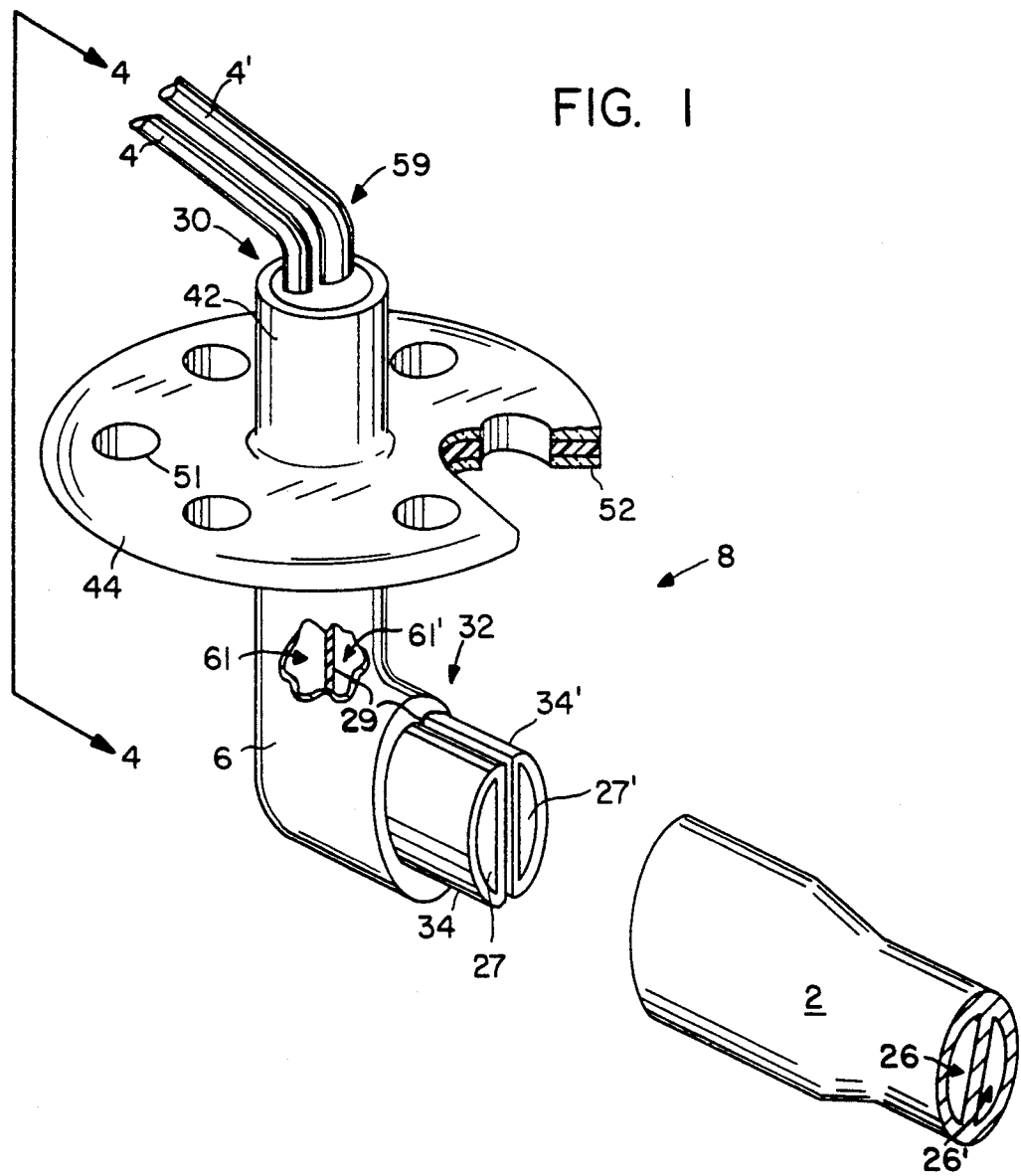
FIG. 1 is an exploded perspective view of the apparatus of the present invention showing the externally located infusion and withdrawal tubes, the percutaneous access device in partial cross-section, the transition device, and the trailing end of the multi-lumen catheter in partial cross-section.

Referring to FIG. 1, the broadest aspects of the invention include a multi-lumen tube 2, externally located infusion and withdrawal tubes 4, 4' and a transition device 6 to couple the multi-lumen tube 2 to the externally located infusion and withdrawal tubes 4, 4'.

Figure 2A:
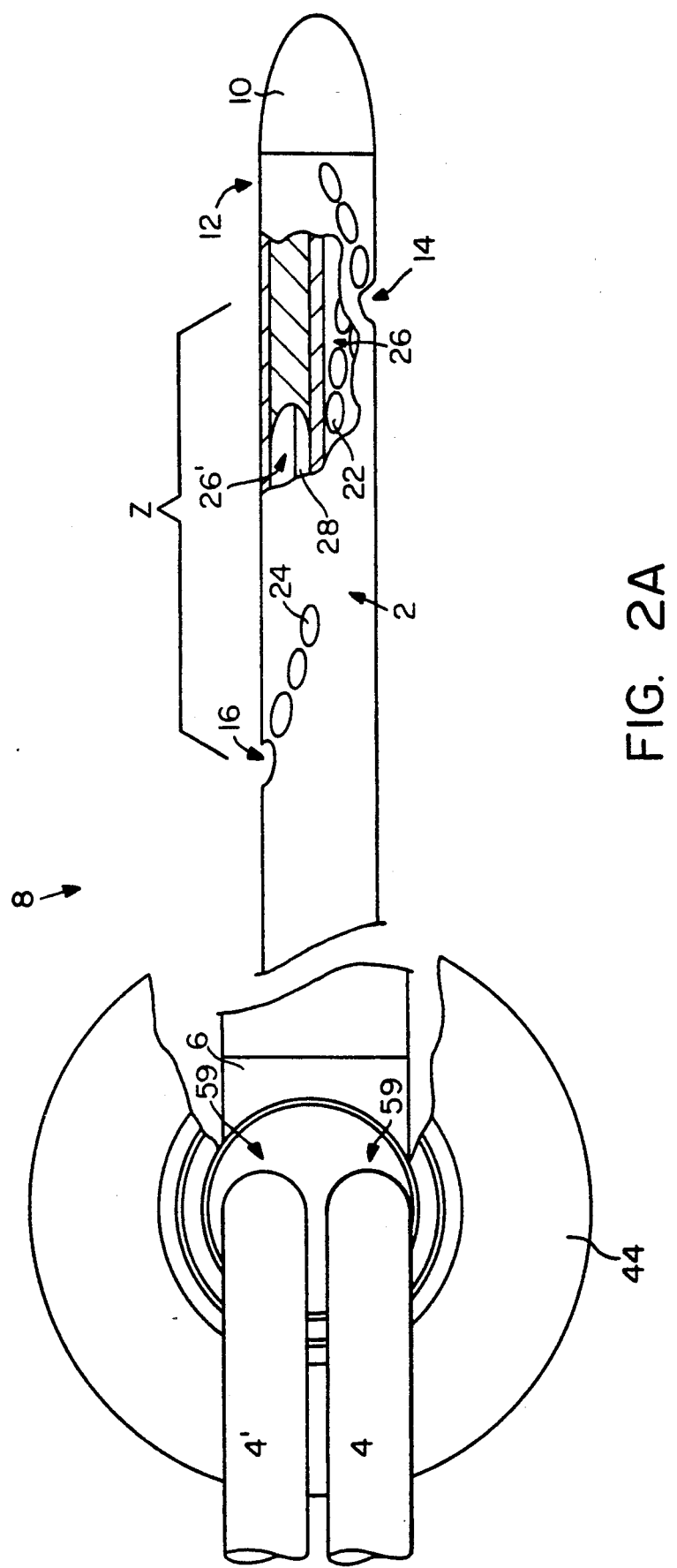
FIG. 2A is a top plan view of the apparatus of the present invention showing the externally located infusion and withdrawal tubes, the percutaneous access device, the transition device, the infusion and withdrawal ports, and the leading end of the catheter in partial cross-section.

As shown in FIG. 2A, the multi-lumen catheter 8 of the present invention has an ellipsoidally shaped tip 10 at a leading end 12 of the multi-lumen tube 2. The elliptical profile of the tip 10 prevents irritation of endothelial cells and thrombus formation within a vessel. The ellipsoidal shape of the tip 10 reduces the potential for thrombosis by reducing the area of stagnation at the end of the tip 10.

Figure 9:
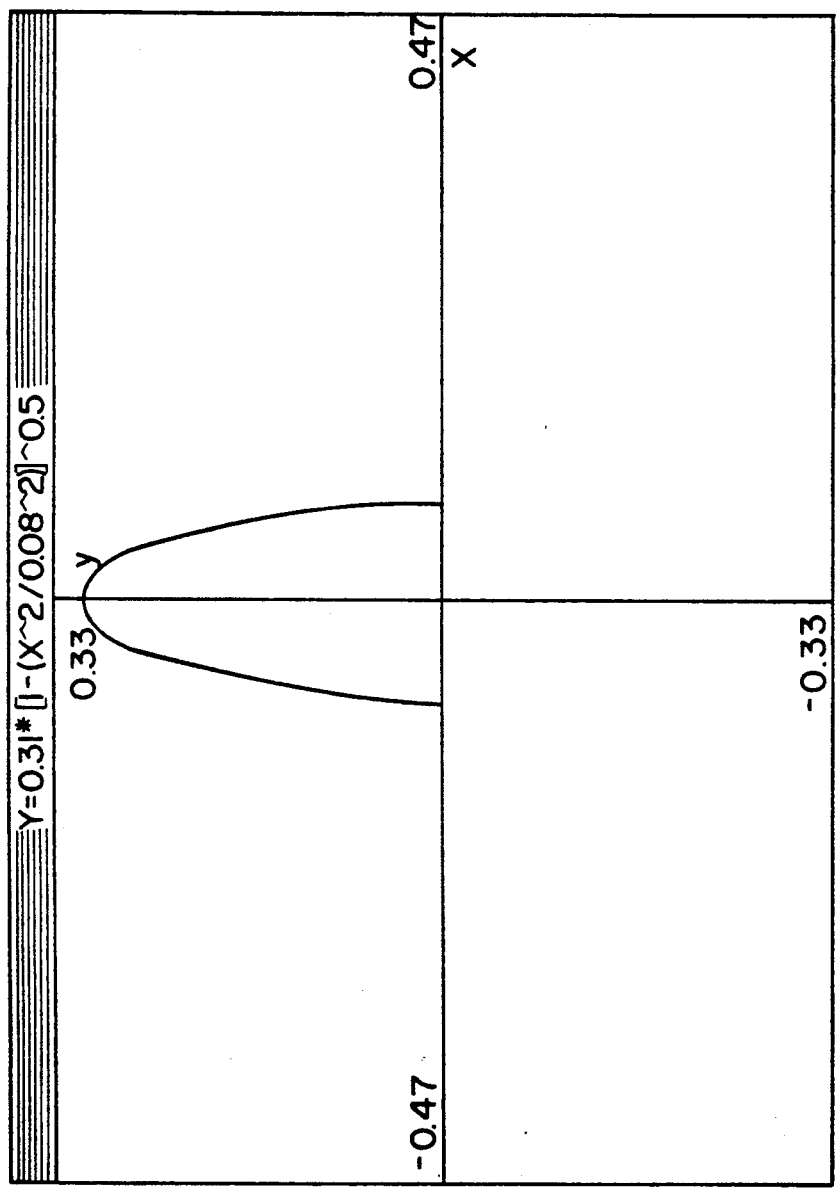
FIG. 9 is a graph of the formula $$Y = 0.31(1 - (X^{2/0.082}))^{\frac{1}{2}}$$

The profile of the tip 10 satisfies the general formula $$Y = 0.31(1 - (X^2/0.08^2))^{\frac{1}{2}}$$

where X and Y refer to distances along two-dimensional axes. This formula describes half an ellipse with a major to minor axis ratio of 1:4 as shown in FIG. 9. Once the tip 10 is designed, it can be molded to the distal end 12 of the multi-lumen tube 2.

The smooth and solid surface of the tip 10 necessitates alternative locations for infusing and withdrawing fluids. In the embodiment shown in FIG. 2A, seven infusion ports 14 and seven withdrawal ports 16 (three ports are not shown) are space each of the internal lumens 26, 26' of the multi-lumen tube 2. The multi-lumen tube 2 shown in FIG. 2A contains an infusion lumen 26 and a withdrawal lumen 26'. The size and number of the infusion and withdrawal ports 14, 16 must be such that the sum of the area available for fluid flow through the ports at least equals the cross-sectional area available for fluid flow in the infusion and withdrawal lumens 26, 26' respectively.

Communication of fluids leaving and entering the lumens 26, 26' of the multi-lumen tube 2 is avoided by distancing the most proximal port 14 of one lumen 26 from the most distal port 16 of another lumen 26'. By way of example, the infusion port 14 and withdrawal port 16 may be spaced approximately 1.0 to 4.0 cm apart, as indicated by the bracket z in the figure.

In one embodiment, shown in FIG. 2A, the infusion ports and withdrawal ports are located along a helical path of each lumen in a staggered relationship. The number of ports in each lumen may vary from one to seven. In the preferred embodiment shown in FIG. 2B, each lumen has one and only one port 14, 16, respectively.

As shown in FIG. 3, once the leading end 12 is inserted into a patient's vessel 25, in the same direction as the blood flow in that vessel (indicated by the arrow 15), fluids may be infused or withdrawn through the appropriate port. It is important that the infusion port(s) 14 be located distal to the withdrawal port(s) 16 so that the treated blood will not be withdrawn.

The multi-lumen tube 2 can be coupled to externally located infusion and withdrawal tubes 4, 4' with a transition device 6. The transition device 6 of the present invention, best shown in FIGS. 1 and 4, resembles an elbow joint having internal, cylindrical lumens 61, 61' that gradually evolve into lumens 27, 27' having the same shape as the lumens 26, 26' within the multi-lumen tube 2. In the case of a dual lumen tube, the internal cylindrical lumens 61, 61' evolve into two "D-shaped" lumens 27, 27' separated by a septum 29. At an epidermal end 30, the transition device 6 accepts externally located infusion and withdrawal tubes 4, 4'. At a subcutaneous end 32, each lumen 27, 27' forms a nipple 34, 34'. The septum 29 is recessed from the nipples 34, 34' so that the nipples 34, 34' fit snugly within corresponding lumens 26, 26' at the proximal end of the multi-lumen tube 2.

The transition device 6 of the present invention provides a smooth transition between externally located infusion and withdrawal tubes 4, 4' and the multi-lumen tube 2 in order to maintain a consistent hydraulic radius along the fluid path. This is accomplished by providing a gradual transfiguration of the lumens 61, 61' within the transition device 6, for example, from cylindrical to "D-shaped," in order to accommodate the cross-sectional profile of the externally located infusion and withdrawal tubes 4, 4' as well as the cross-sectional profile of the multi-lumen tube 2. In this manner, a tight seal between the transition device 6 and each of the externally located infusion and withdrawal tubes 4, 4' and the multi-lumen tube 2 can be achieved. The size, number, and cross-sectional configuration of the internal lumens within the transition device 6 can be varied to accommodate any number of external tubes having various sizes, numbers of lumens, and cross-sectional configurations.

The transition device 6 reduces the number of tubes passing across a patient's skin and thus reduces the risk of infection. The unique "L-shape" of the transition device 6 further reduces the risk of infection by tunneling the multi-lumen tube 2 through the subcutaneous tissue to a remote site for penetration into a vessel or body cavity. In this manner, infection at the introduction site 38 is reduced and back leakage of the infusing fluids is minimized.

Figure 5A:
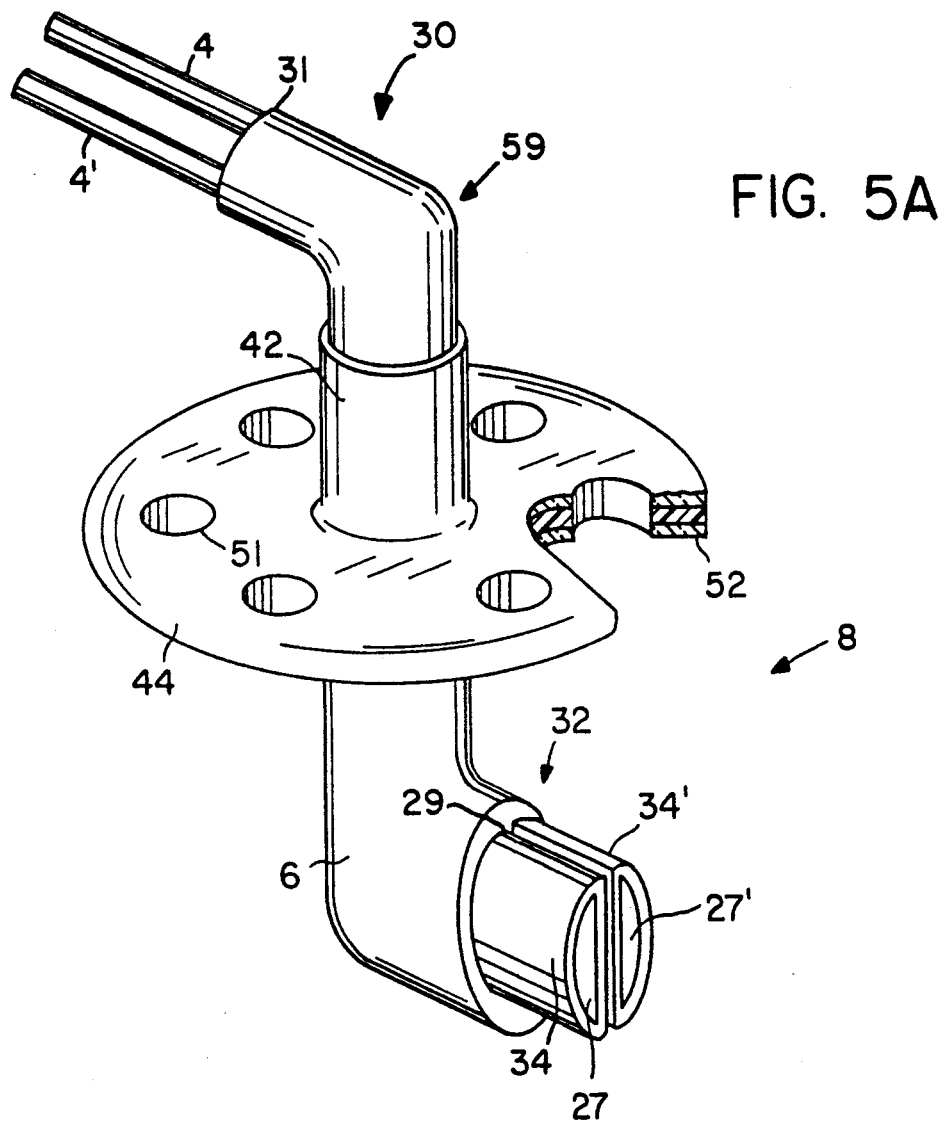
FIG. 5A is a perspective view of an embodiment of the present invention showing the externally located infusion and withdrawal tubes, the percutaneous access device in partial cross-section, and the transition device in partial cross-section with the rigid adaptor forming an upright "Z-shape"

In one important embodiment shown in FIG. 5A, the transition device 6 may have a rigid adapter 31 for providing the sharp bend angle 59 which may be hermetically bonded to the epidermal end 30 of the transition device 6 and to infusion and withdrawal tubes 4, 4' to provide fluid communication with the infusion port 14 and the withdrawal port 16 and rigid support for the tubes 4, 4'. The adapter 31 strengthens the bend angle 59 and avoids breakage. In the embodiment shown in FIG. 5A, the adaptor is bonded to the transition device to form an upright "Z-shape." In another embodiment, shown in FIG. 5B, the transition device 6 and adapter 31 may form a "U-shape." That is, the epidermal end 30 is in fixed parallel relation to the subcutaneous end 32. FIG. 6 shows the embodiment of FIG. 5B in cross-section in a vessel.

The epidermal end 30 of the transition device 6 may be two flexible tubes 4, 4' capable of adapting to either a "U" or an upright "Z" conformation, shown in FIG. 1 in the upright "Z" conformation. It may also be two flexible bellows 60, 60' capable of adapting to either a "U" or an upright "Z" conformation, shown in FIG. 7 in the "U" conformation. Finally, it may be embodied as a rigid adapter 31 connected to two tubes 4, 4' and connected to the transition device 6 in either an upright "Z" (FIG. 5A) or a "U" (FIG. 5B) conformation. What is important is that the tubes 4, 4' run parallel to the multi-lumen tube, and not in a straight line in alignment with the introduction site in order to substantially decrease the risk of infection.

Another barrier to infection at the introduction site 38 can be erected by permanently bonding the transition device 6 to the inner diameter of a percutaneous access device (PAD) 40. A preferred long-term percutaneous access device 40 shown and described herein overcomes the fundamental biological and mechanical instability of known devices by controlling epidermal cell downgrowth and promoting the formation of a tight barrier to infection at the skin surface. The biologic barrier or seal is the result of the use of the percutaneous access device of the type set forth in U.S. Pat. No. 4,886,502 the teachings of which are incorporated herein by reference.

The percutaneous access device 40, shown in FIGS. 1 and 4, resembles a button having a raised neck 42 with a central hole or bore therethrough of a diameter just sufficient to accommodate the transition device 6. The PAD 40 includes a generally flat skirt 44 and a neck 42, preferably integral with and substantially normal to the skirt 44. Both the skirt 44 and the neck 42 are formed of a nontoxic biocompatible material such as a semirigid polyurethane and are sized such that when the PAD 40 is implanted, its neck 42 penetrates the epidermal 46 and dermal 48 layers and its skirt 44 is anchored in the subcutaneous tissue 50. A suitable polyurethane is Tecoflex EG-60D, available from Thermedics Inc. of Woburn, Mass.

In a preferred embodiment, the skirt 44 is disk-shaped and has a diameter in the range of about 0.8 to 1.8 inches and a thickness of about 0.010 to 0.100 inches. One or more holes 51 are provided in the skirt 44 to encourage tissue penetration for increased anchoring of the PAD 40 as well as to encourage lymphatic drainage. The neck 42 has a diameter of about 0.125 to 0.50 inches and flares upward from the skirt 44 to a distance of about 0.08 to 0.40 inches so as to extend through the epidermal 46 and dermal 48 layers of a patient when the skirt 44 is implanted in the subcutaneous tissue 50. A central hole or bore is provided in the neck 42 and also extends through the skirt 44 to accommodate the transition device 6.

To promote the healing of a patient's skin and the formation of a tight, infection-free barrier between the percutaneous access device 40 and adjacent tissues following implantation of the PAD 40, the skirt 44 and the neck 42 are covered by a porous material 52. A suitable porous material 52 is Dermaport, available from Thermedics Inc. The porous material 52 is tightly bonded to the underlying skirt 44 and neck 42 by a suitable adhesive such as No. 1-MP polyurethane adhesive available from Thermedics Inc.

In another embodiment, shown in FIG. 4, the skirt 44 and at least the lower portion of the neck 42 are covered by a two-stage porous bed. A first stage 54 of the bed overlies the lower portion of the neck 42, preferably commencing at a location such that the top of this first stage 54 is positioned at the epidermal layer 46 when the PAD 40 is implanted. The first stage 54 may also extend along part of the upper surface of the skirt 44, e.g., a distance of up to 0.25 inches, terminating at a junction 56 formed between adjacent ends of the first stage 54 and a second stage 58. The junction 56 between the first stage 54 and second 58 stage can also be positioned at the point where the neck 42 meets the skirt 44.

A material for the first stage 54 of the porous bed can be polytetrafluoroethylene (PTFE) having pore sizes of about 50-125 microns and a thickness of about 0.020 inches. For example, the first stage 54 of the porous bed may be made of Impra 15:1, a PTFE material available from Impra Inc. of Tempe, Ariz., and formed by extrusion followed by stretching to fifteen times the extruded length.

The second stage 58 of the porous bed covers at least the remainder of the upper surface of the skirt 44 and, preferably, the lower surface as well. This stage 58 of the porous bed may be formed of a material such as a polyester velour, e g., Dacron velour available as part No. 600K61121 from the United States Catheter and Instrument Company of Glenfalls, N.Y. This material is a woven fabric with loose strands to allow for cell infiltration, and its pore sizes are considerably larger than those of the first stage 54 of the porous bed, typical values being about 100-800 microns.

The first stage 54 and second stage 58 of the porous bed may, instead, be fabricated of multiple layers of filaments of a polyurethane such as Tecoflex EG-60D, available from Thermedics Inc. of Woburn, Mass. (Tecoflex is a registered trademark of Thermedics for medical grade urethane elastomeric materials). This material may be formed and the stages of the porous bed may be fabricated as described in U.S. Pat. No. 4,668,222, the teachings of which are incorporated herein by reference.

Both porous stages 54, 58 are tightly bonded to the underlying substrate, the skirt 44 and the neck 42, by a suitable adhesive such as No. 1-MP polyurethane adhesive available from Thermedics Inc. To improve its biocompatibility, the Dacron velour may be chemically stripped, as by washing it in distilled water adjusted to a pH of 10.

It is essential to the successful long-term implantation of the percutaneous access device 40 of the invention that the path length of the first stage 54 of the porous bed along the neck 42 and the skirt 44, and the pore sizes of both the first and the second stages 54, 58, repectively, be properly selected to fulfill the different functions performed by these stages. Accordingly, the material of the first stage 54 has pores of about 75-400 microns in size, preferably about 75-125 microns, a size which permits downgrowth of epidermal cells, but at a rate far less than that which would occur in a material having larger pores. The biomaterial of the second stage 58 has pores of about 75 to 800 microns in size, large enough to allow penetration and viability of cells such as fibroblasts which displace body fluids from the pores and synthesize collagen. The controlled rate of epidermal cell downgrowth allowed by a first stage length of about 0.25 inches, is sufficient to prevent epidermal cells from reaching the junction 56 until mature collagen is formed in the pores of the second stag 58 (typically two to six months following implantation of the device). The presence of mature collagen in the second stage 58 terminates the growth of epidermal cells at or near the junction 56, thus forming a stable, tight, dermal/biomaterial barrier.

For purposes of the invention described and claimed herein, pore size is defined as the diameter of a circle whose area is equal to the area of an equivalent opening or void in the bed structures. The pores may, for example, be formed between threads or filaments of the porous bed structures, the filaments preferably being utilized in multiple layers positioned to avoid alignment of pores in adjacent layers. The resulting structure of the porous bed stages 54, 58 has voids or pores which are interconnected along the length of the bed, permitting controlled growth of cells into the pores and strong mechanical bonding due to wrapping of cells and connective tissue around and in between the filaments. It is essential that the pores be interconnected so that collagen may be deposited and inhibit downgrowth of the epidermal cells. The necessity of proper pore size selection and of a two-stage bed of porous material is discussed in co-pending, U.S. Pat. No. 4,886,502 filed Dec. 9, 1986 by Poirier et al., the teachings of which are incorporated herein by reference.

To assemble the multi-lumen catheter 8 of the present invention, the epidermal end 30 of the transition device 6 is fed through the central bore of the skirt 44 of the percutaneous access device 40 until it is flush with the neck 42. A permanent seal or bond of the PAD 40 to the transition device 6 can be accomplished by using an adhesive such as 1-MP polyurethane adhesive available from Thermedics, Inc. Externally located infusion and withdrawal tubes 4, 4' can be inserted into the internal lumens 61, 61' at the epidermal end 30 of the transition device 6, while the multi-lumen tube 2 is inserted over the nipples 34, 34' at the subcutaneous end 32 of the transition device 6. These junctions can be sealed also using an adhesive such as 1-PP polyurethane available from Thermedics Inc.

In one embodiment, shown in FIG. 4, the externally located infusion and withdrawal tubes 4, 4' are fabricated with a sharp bend angle 59 of approximately ninety degrees. One method of accomplishing this sharp bend angle 59 is by placing the tube on an appropriately-shaped mandrel and heat forming the tube. This configuration permits the external tubes 4, 4' to run parallel to the dermal layer 48 and to the multi-lumen tube 2 in either a "U-shape" or an upright "Z-shape."

Figure 7:
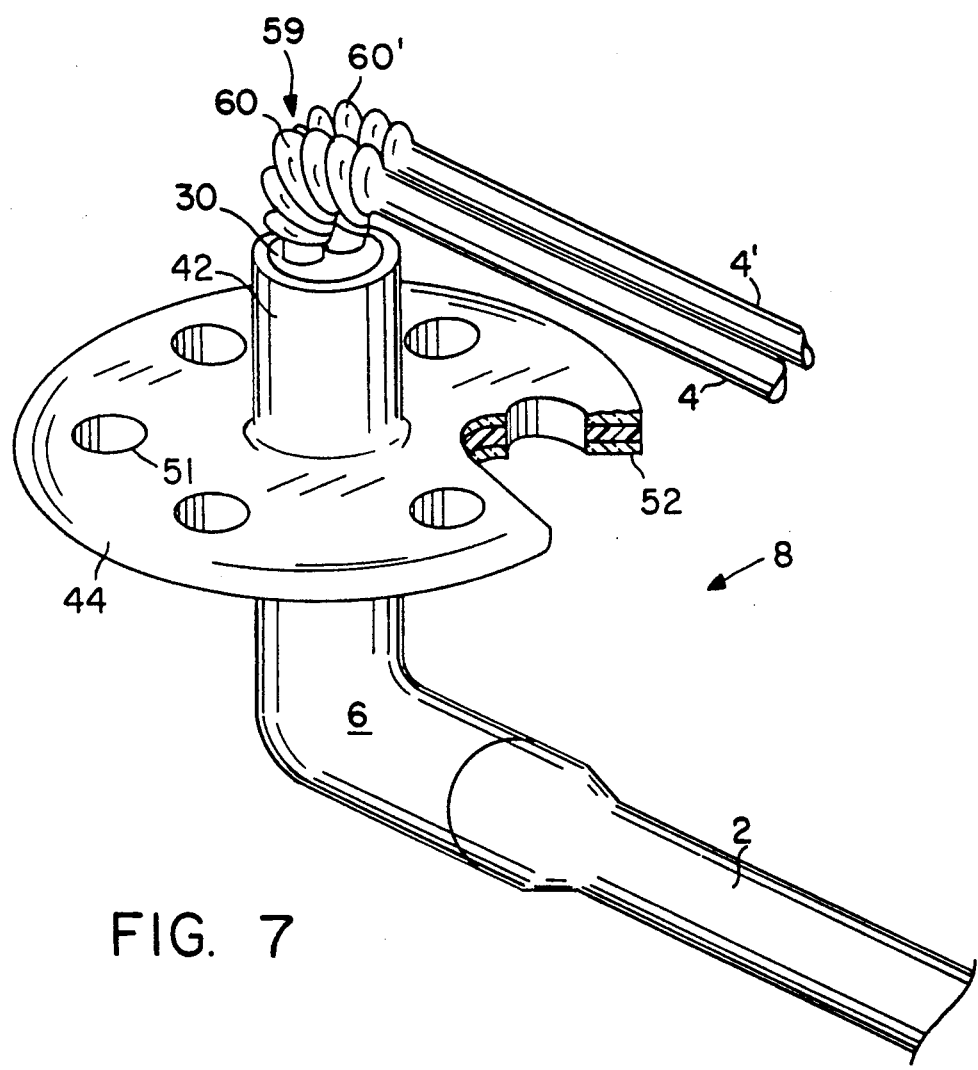
FIG. 7 is a side plan view of an embodiment of the of a multi-lumen catheter according to the invention showing the bellows section of the externally located infusion and withdrawal tubes.

In another embodiment, shown in FIG. 7, the externally located infusion and withdrawal tubes 4, 4' include accordian-pleated bellows sections 60, 60' as described in co-pending U.S. patent application Ser. No. 939,748. The bellows section 60 functions as a shock absorber to reduce the incidence of trauma to the introduction site 38 and to relieve any stress the PAD 40 or the multi-lumen tube 2 might receive from movement of the externally located infusion and withdrawal tubes 4, 4'. The bellows section also allows the externally located infusion and withdrawal tubes 4, 4' to be at an approximately ninety degree angle with respect to the neck 42 of the PAD 40 such that either a "U-shape" or an upright "Z-shape" is formed without restricting the fluid flow within the tubes 4, 4' and without exerting any pressure on the PAD 40.

In a third embodiment, shown in FIGS. 5A & B, the externally located infusion and withdrawal tubes 4, 4' may be inserted into a rigid adapter 31 to form the sharp bend angle 59. The adapter 31 may in turn be hermetically bonded to the transitions device 6, forming a continuous path for fluid flow among the tubes 4, 4' and the internal lumens 61, 61' of the transition device 6, and the lumens 26, 26' of the multi-lumen tube 2. The adapter 31 functions to provide support and to prevent breakage, and allows the externally located tubes 4, 4' to be at an approximately 90° angle with respect to the neck 42 of the PAD 40 without restricting the fluid flow within the catheter, and without exerting any pressure on the PAD 40. The adapter 31 may be bonded to the transition device 6 to form either a "U-shape" or an upright "Z-shape."

Figure 8:
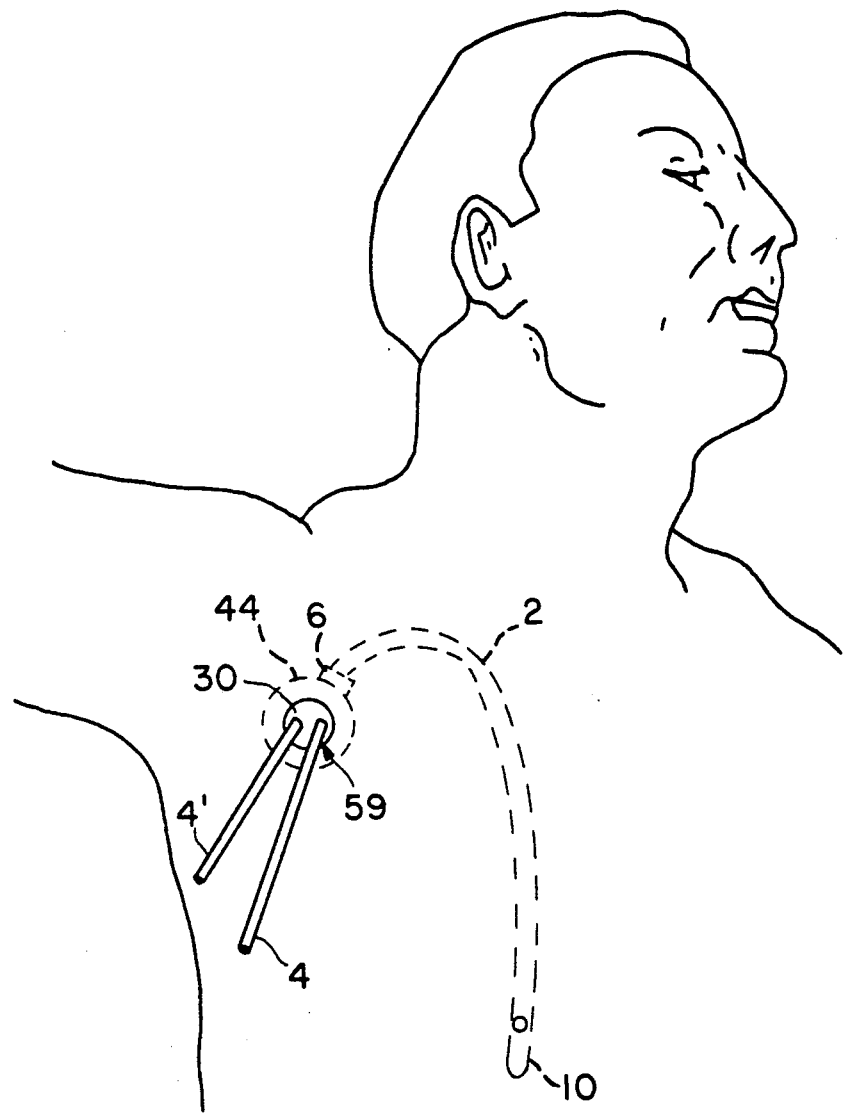
FIG. 8 is a diagrammatic view of an embodiment of a multi-lumen catheter according to the invention in a patient.

Referring to FIG. 8, the procedure for implantation of the multi-lumen catheter of the present invention is accomplished in a two step approach. Initially, the transition device 6 is implanted through a subcutaneous tunnel terminating at an exit site just superior to the mammary gland. Once the catheter is implanted within the hypodermis, the leading end of the catheter is inserted into the subclavian vein or jugular vein by first puncturing the hypodermal layer with a needle and advancing the needle into the blood vessel. A guide wire is then passed through the needle. The needle is then removed and replaced with a dilator and sheath which is advanced into the vessel. The dilator is removed and the catheter tip is inserted into the sheath and advanced. Fluoroscopy and radiographic techniques can be used to establish proper positioning and catheter tip placement. After the catheter is properly positioned, the sheath can be removed and the incision closed in normal fashion.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalents thereof. Hence, it is recognized that various modifications are possible when within the scope of the present invention as claimed.

What is claimed is:

1. A transition device for providing fluid communication between a multi-lumen tube and an externally located infusion or withdrawal tube comprising:
    a tube having a first epidermal end which emerges from the epidermis of a patient into the external environment when the transition device is in place and a second subcutaneous end which is perpendicular to said first end and which is implanted int he patient when the transition device is in place;
    said subcutáneous end terminating in two D-shaped nipples arranged in a circular conformation such that a cylindrical multi-lumen tube having a similar circular conformation may be fitted hermetically to said subcutaneous end over said nipples;
    two lumens running through the interior of said tube, said lumens being separated by a septum, said septum being recessed from said nipples;
    wherein each of said two lumens is capable of accepting an externally located cylindrical infusion or withdrawal tube at said epidermal end and of maintaining a consistent hydraulic radius along the fluid path of the tube between the infusion or withdrawal tube and the multi-lumen tube.

2. The transition device of claim 1 having bonded thereto a percutaneous access device for long term skin penetration, said percutaneous access device comprising a neck for protrusion through the skin of a patient and a skirt for anchoring the transition device into subcutaneous tissue.

3. The transition device of claim 2 wherein said neck and said skirt are covered by a porous material.

4. A transition device for providing fluid communication between a multi-lumen tube and an externally located infusion or withdrawal tube comprising:
    a tube having a first epidermal end which emerges from the epidermis of a patient into the external environment when the transition device is in place and a second subcutaneous end which is perpendicular to said first end and which is implanted int he patient when the transition device is in place;
    said subcutaneous end terminating in multiple nipples arranged in a circular conformation such that a cylindrical multi-lumen tube having a similar conformation may be fitted hermetically to said subcutaneous end over said nipples;
    multiple lumens running through the interior of said tube, said multiple lumens being separated by septa, said septa being recessed from said nipples;
    and wherein each of said multiple lumens is capable of being fluidly connected to a separate lumen in the multi-lumen tube;
    and wherein each of said multiple lumens is configured to be capable of accepting an externally located cylindrical infusion or withdrawal tube at said epidermal end and of maintaining a consistent hydraulic radius along the fluid path between said infusion or withdrawal tube and the multi-lumen tube.

5. A transition device for providing fluid communication between a multi-lumen tube and an externally located infusion or withdrawal tube comprising:
    a cylindrical multi-lumen tube;
    an infusion or withdrawal tube;
    a tube having a first epidermal end which emerges from the epidermis of a patient into the external environment when the transition device is in place and a second subcutaneous end which is perpendicular to said first end and which is implanted in the patient when the transition device is in place;
    said subcutaneous end terminating in two D-shaped nipples arranged in a circular conformation such that the cylindrical multi-lumen tube may be fitted hermetically to said subcutaneous end over said nipples;

two lumens running through the interior of said tube, said lumens being separated by a septum, said septum being recessed from said nipples;

each of said lumens being capable of accepting the cylindrical infusion or withdrawal tube at said epidermal end, the cylindrical infusion or withdrawal tube positioned to rest perpendicular to the epidermis of the patient and each of said lumens being configured to maintain a consistent hydraulic radius along the fluid path of the tube between the infusion or withdrawal tube and the multi-lumen tube.

6. The transition device of claim 5 having bonded thereto a percutaneous access device for long term skin penetration, said percutaneous access device comprising a neck for protusion through the skin of a patient and a skirt for anchoring the transition device into subcutaneous tissue.

7. The transition device of claim 6 wherein said neck and said skirt are covered by a porous material.

8. A transition device for providing fluid communication between a multi-lumen tube and an externally located infusion or withdrawal tube comprising:

a multi-lumen tube;

an infusion or withdrawal tube;

a tube having a first epidermal end which emerges from the epidermis of a patient into the external environment when the transition device is in place and a second subcutaneous end which is perpendicular to said first end and which is implanted in the patient when the transition device is in place;

said subcutaneous end terminating in multiple nipples arranged in a circular conformation such that said cylindrical multi-lumen tube may be fitted hermetically to said subcutaneous end over said nipples;

multiple lumens running through the interior of said tube, said multiple lumens being separated by septa, said septa being recessed from said nipples and wherein each of said multiple lumens is capable of being fluidly connected to a separate lumen in the multi-lumen tube;

each of said lumens being configured to be capable of accepting the cylindrical infusion or withdrawal tube at said epidermal end and of maintaining a consistent hydraulic radius along the fluid path between said infusion or withdrawal tube and the multi-lumen tube;

the cylindrical infusion of withdrawal tube positioned to rest perpendicular to the epidermis of the patient.

* * * * *